United States Patent
Mahmud

(10) Patent No.: US 11,631,498 B2
(45) Date of Patent: Apr. 18, 2023

(54) METHODS AND SYSTEMS FOR PREVENTING AND REVERSING OSTEOPOROSIS

(71) Applicant: Taher Mahmud, London (GB)

(72) Inventor: Taher Mahmud, London (GB)

(73) Assignee: Taher Mahmud, London (GB)

( * ) Notice: Subject to any disclaimer, the term of this patent is extended or adjusted under 35 U.S.C. 154(b) by 0 days.

(21) Appl. No.: 17/477,730

(22) Filed: Sep. 17, 2021

(65) Prior Publication Data

US 2022/0093254 A1 Mar. 24, 2022

Related U.S. Application Data

(60) Provisional application No. 63/080,464, filed on Sep. 18, 2020.

(51) Int. Cl.
| | | |
|---|---|---|
| *G16H 50/20* | (2018.01) | |
| *G16H 20/10* | (2018.01) | |
| *A61P 19/10* | (2006.01) | |
| *G16H 50/30* | (2018.01) | |
| *A61B 5/00* | (2006.01) | |
| *G16H 10/40* | (2018.01) | |

(52) U.S. Cl.
CPC ............ *G16H 50/20* (2018.01); *A61B 5/4509* (2013.01); *A61P 19/10* (2018.01); *G16H 10/40* (2018.01); *G16H 20/10* (2018.01); *G16H 50/30* (2018.01)

(58) Field of Classification Search
CPC ....... A61B 5/4509; A61P 19/10; G16H 10/40; G16H 20/10; G16H 50/20; G16H 50/30
See application file for complete search history.

(56) References Cited

U.S. PATENT DOCUMENTS

| | | | | |
|---|---|---|---|---|
| 10,832,822 B1 * | 11/2020 | Neumann | .............. | G16H 50/20 |
| 2007/0208597 A1 * | 9/2007 | Recknor | ................ | G16H 50/30 |
| | | | | 705/3 |

(Continued)

FOREIGN PATENT DOCUMENTS

| | | | | |
|---|---|---|---|---|
| JP | 2004065696 A | * | 3/2004 | |
| WO | WO-2014153661 A1 | * | 10/2014 | ........... C09B 23/083 |

OTHER PUBLICATIONS

Hurra, Tanveer. "Decision Trees—How to draw them on paper", Apr. 4, 2020, Towards Data Science (Year: 2020).*

*Primary Examiner* — Patrick Fernandes
*Assistant Examiner* — Anna Roberts
(74) *Attorney, Agent, or Firm* — Caldwell Intellectual Property Law

(57) ABSTRACT

In an aspect a system for osteoporosis monitoring is presented. A system includes a computing device. A computing device is configured to measure osseous tissue data of a user through an osseous measurement device. A computing device is configured to determine a current osteoporosis state of a user as a function of measured osseous tissue data of a user. A computing device is configured to predict an advancement of a current state of osteoporosis of a user. A computing device is configured to generate an osteoporosis recovery program for the user. A computing device is configured to display an osteoporosis recovery program to a user. A computing device is configured to receive, through a remote computing device, physiological data of a user. A computing device is configured to update an osteoporosis recovery program.

20 Claims, 6 Drawing Sheets

(56) References Cited

U.S. PATENT DOCUMENTS

2009/0234251 A1* 9/2009 Bhattacharya ....... A61B 5/7257
600/595
2018/0247020 A1* 8/2018 Itu .......................... G16H 10/60
2019/0336097 A1* 11/2019 Bregman-Amitai ... G06K 9/627

* cited by examiner

METHODS AND SYSTEMS FOR PREVENTING AND REVERSING OSTEOPOROSIS

CROSS-REFERENCE TO RELATED APPLICATIONS

This application claims the benefit of priority of U.S. Provisional Patent Application Ser. No. 63/080,464, filed on Sep. 18, 2020, and titled "Methods and Systems for Preventing and Reversing Osteoporosis," which is incorporated by reference herein in its entirety.

FIELD OF THE INVENTION

The present invention generally relates to the field of osteoporosis monitoring. In particular, the present invention is directed to systems and methods for osteoporosis monitoring.

BACKGROUND

Osteoporosis is a condition where bones become fragile and if untreated, osteoporosis can progress painlessly until a bone may break. Individuals often first become aware of osteoporosis after an initial fracture. However, many individuals may not have clear symptoms or ignore the warning signs of a fracture due to osteoporosis until a more serious bone break. As such, modern systems for osteoporosis monitoring can be improved.

SUMMARY OF THE DISCLOSURE

In an aspect a system for osteoporosis monitoring is presented. A system includes a computing device. A computing device is configured to measure osseous tissue data of a user through an osseous measurement device. A computing device is configured to determine a current osteoporosis state of a user as a function of measured osseous tissue data of a user. A computing device is configured to predict an advancement of a current state of osteoporosis of a user as a function of osseous tissue data of a user and a current osteoporosis state of the user. Predicting includes receiving training data. Training data includes osseous tissue data correlated to stages of osteoporosis. Predicting includes training a machine learning process with training data. A machine learning process, responsive to training, is configured to input osseous tissue data and output a predicted advancement of osteoporosis of a user. A computing device is configured to generate as a function of a predicted advancement of osteoporosis of a user, measured osseous data of a user, and a current osteoporosis state of the user, an osteoporosis recovery program for the user. A computing device is configured to display an osteoporosis recovery program to a user on an interactive graphical user interface of a remote computing device. A computing device is configured to receive, through a remote computing device, physiological data of a user. A computing device is configured to update an osteoporosis recovery program as a function of physiological data of a user.

In another aspect a method of osteoporosis monitoring is presented. A method includes measuring, through an osseous tissue measurement device, osseous tissue data of a user. A method includes determining, at a computing device, a current osteoporosis state of a user as a function of osseous tissue data of a user. A method includes predicting, at a computing device, an advancement of a current state of osteoporosis of a user as a function of osseous tissue data and a current osteoporosis state of the user. Predicting includes receiving training data correlating osseous tissue data to stages of osteoporosis. Predicting includes training a machine learning process with training data. A machine learning process, response to training, is configured to input osseous tissue data and output a predicted advance of osteoporosis of a user. A method includes generating, at a computing device, an osteoporosis recovery program for a user. An osteoporosis recovery program is generated as a function of a predicted advancement of osteoporosis of a user, measured osseous tissue data of the user, and a current osteoporosis state of the user. A method includes displaying an osteoporosis recovery program to a user on an interactive graphical user interface of a remote computing device. A method includes receiving, through a remote computing device, physiological data of a user. A method includes updating an osteoporosis recovery program as a function of physiological data of a user.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

Figure 1:
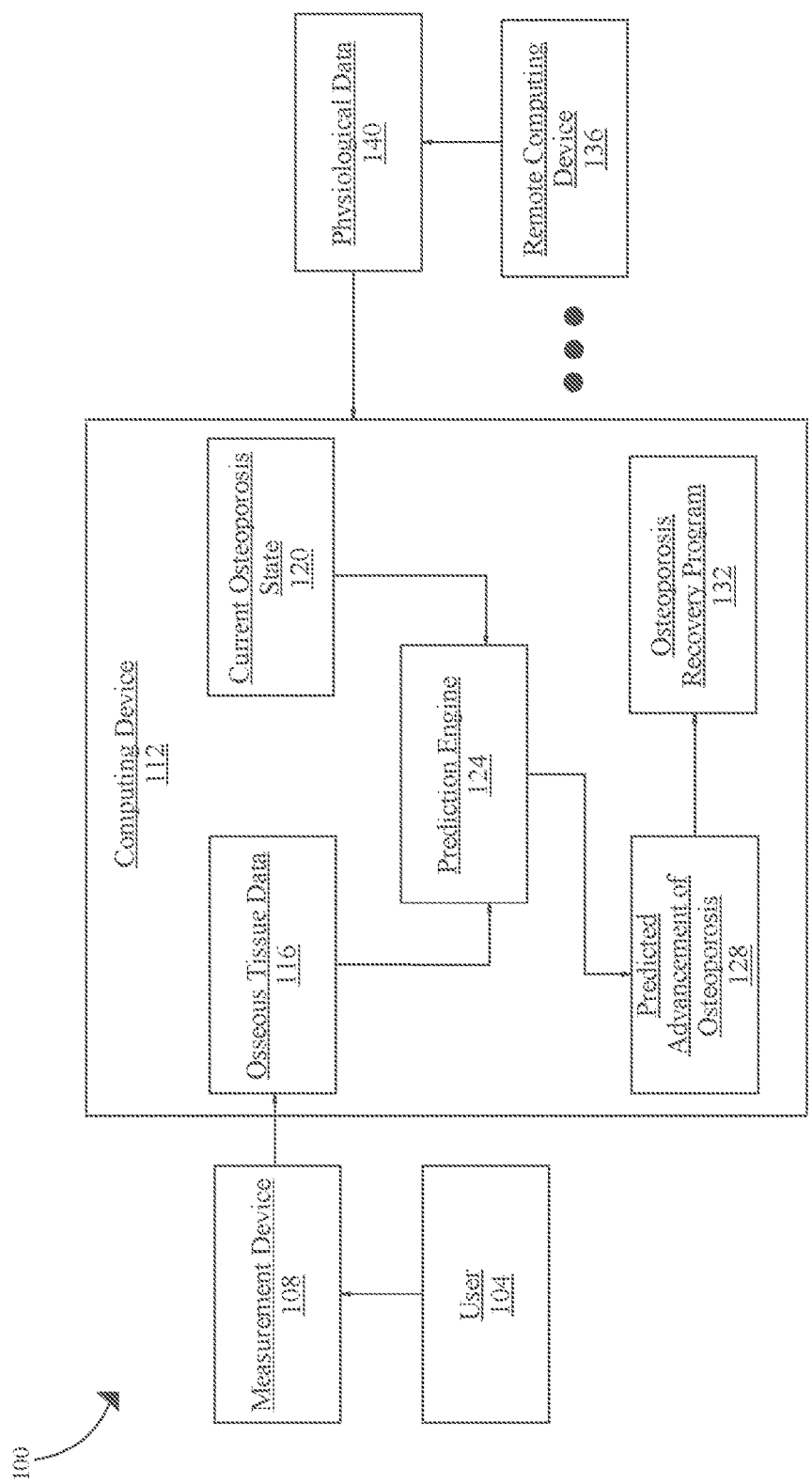
FIG. 1 is a block diagram illustrating a system of osteoporosis monitoring.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Described herein is a system for osteoporosis monitoring. A system may include a computing device. A computing device may be configured to measure osseous tissue data of a user through an osseous measurement device. A computing device may be configured to determine a current osteoporosis state of a user as a function of measured osseous tissue data of a user. A computing device may be configured to predict an advancement of a current state of osteoporosis of a user as a function of osseous tissue data of a user and a current osteoporosis state of the user. Predicting may include receiving training data. Training data may include osseous tissue data correlated to stages of osteoporosis. Predicting may include training a machine learning process with training data. A machine learning process, responsive to training, may be configured to input osseous tissue data and output a predicted advancement of a stage of osteoporosis of a user. A computing device may be configured to generate as a function of a predicted advancement of a stage of osteoporosis of a user, measured osseous data of a user, and a current osteoporosis state of the user, an osteoporosis recovery program for the user. A computing device may be configured to display an osteoporosis recovery program to a user on an interactive graphical user interface of a remote computing device. A computing device may be configured to receive, through a remote computing device, physiological data of a user. A computing device may be configured to update an osteoporosis recovery program as a function of physiological data of a user.

Described herein is a method of osteoporosis monitoring. A method may include measuring, through an osseous tissue measurement device, osseous tissue data of a user. A method may include determining, at a computing device, a current osteoporosis state of a user as a function of osseous tissue data of a user. A method may include predicting, at a computing device, an advancement of a current state of osteoporosis of a user as a function of osseous tissue data and a current osteoporosis state of the user. Predicting may include receiving training data correlating osseous tissue data to stages of osteoporosis. Predicting may include training a machine learning process with training data. A machine learning process, response to training, may be configured to input osseous tissue data and output a predicted advance of a stage of osteoporosis of a user. A method may include generating, at a computing device, an osteoporosis recovery program for a user. An osteoporosis recovery program may be generated as a function of a predicted advancement of a stage of osteoporosis of a user, measured osseous tissue data of the user, and a current osteoporosis state of the user. A method may include displaying an osteoporosis recovery program to a user on an interactive graphical user interface of a remote computing device. A method may include receiving, through a remote computing device, physiological data of a user. A method may include updating an osteoporosis recovery program as a function of physiological data of a user.

Referring now to FIG. 1, an exemplary embodiment of a system 100 for osteoporosis monitoring is illustrated. System 100 may include computing device 112. Computing device 112 may include any computing device as described in this disclosure, including without limitation a microcontroller, microprocessor, digital signal processor (DSP) and/or system on a chip (SoC) as described in this disclosure. Computing device 112 may include, be included in, and/or communicate with a mobile device such as a mobile telephone or smartphone. Computing device 112 may include a single computing device operating independently, or may include two or more computing device operating in concert, in parallel, sequentially or the like; two or more computing devices may be included together in a single computing device or in two or more computing devices. Computing device 112 may interface or communicate with one or more additional devices as described below in further detail via a network interface device. Network interface device may be utilized for connecting computing device 112 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 112 may include but is not limited to, for example, a computing device or cluster of computing devices in a first location and a second computing device or cluster of computing devices in a second location. Computing device 112 may include one or more computing devices dedicated to data storage, security, distribution of traffic for load balancing, and the like. Computing device 112 may distribute one or more computing tasks as described below across a plurality of computing devices of computing device, which may operate in parallel, in series, redundantly, or in any other manner used for distribution of tasks or memory between computing devices. Computing device 112 may be implemented using a "shared nothing" architecture in which data is cached at the worker, in an embodiment, this may enable scalability of system 100 and/or computing device.

With continued reference to FIG. 1, [computing device 112 may be designed and/or configured to perform any method, method step, or sequence of method steps in any embodiment described in this disclosure, in any order and with any degree of repetition. For instance, computing device 112 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 112 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, system 100 may include measurement device 108. Measurement device 108 may include one or more sensors. In some embodiments, measurement device 108 may include motion sensors, such as, but not limited to, accelerometers, gyroscopes, inertial measurement units (IMU), and the like. Measurement device 108 may be configured to measure a motion of user 104. In some embodiments, measurement device 108 may be configured to measure a mobility of user 104. A "mobility" as used in this disclosure is the ability to be moved easily. In some embodiments, measuring a mobility of user 104 may include measuring one or more movements of user 104, such as, but not limited to, walking, running, bending over, standing up, and the like. In some embodiments, measurement device 108 may be configured to measure bone density of user 104. Measurement device 108 may include a scanning device that may be configured to measure a bone density of user 104. In some embodiments, measurement device 108 may include, but is not limited to, dual-energy x-ray absorptiometry systems (DXA or DEXA), Dual x-ray Absorptiometry and Laser (DXL), Quantitative computed tomography (QCT), Quantitative ultrasound (QUS), Single photon absorptiometry (SPA), Dual photon absorptiometry (DPA), digital x-ray radiogrammetry (DXR), and/or single energy x-ray absorptiometry (SEXA). In some embodiments, measurement device 108 may be configured to measure a bone mineral density (BMD) of user 104.

Still referring to FIG. 1, measurement device 108 may be configured to transmit osseous tissue data 116 to computing device 112. In some embodiments, measurement device 108 may transmit osseous tissue data 116 to computing device 112 over a wireless connection. Communication generally be performed using any direct or indirect form of electronic communication, including without limitation, communication via a network such as a local area network, wide area network, the Internet, or the like. In other embodiments, measurement device 108 may transmit osseous tissue data 116 to computing device 112 through a wired connection. "Osseous tissue data" as used in this disclosure is any data pertaining to bone structures. Osseous tissue data 116 may include, but is not limited to, bone mineral density, bone mobility, bone weight, bone strength, bone thickness, bone fragility, bone brittleness, and the like. In some embodiments, computing device 112 may be configured to determine current osteoporosis state 120. Computing device 112 may determine current osteoporosis state 120 as a function of osseous tissue data 116. In some embodiments, computing device 112 may communicate with an osseous tissue database. An osseous tissue database may be as described below in FIG. 2. In some embodiments, computing device 112 may communicate with an osseous tissue database to extract osseous tissue data 116 of user 104. In some embodiments, computing device 112 may use an osteoporosis state machine learning model. An osteoporosis state machine learning model may be configured to input osseous tissue data and output a state determination of osteoporosis of a user. An osteoporosis state machine learning model may be trained using training data correlating osseous tissue data to osteoporosis states. In some embodiments, training data may be selected and/or filtered using a training data classifier. A training data classifier may be configured to classify one or more users to a cohort of similar users. In a non-limiting example, a training data classifier may classify a user to a cohort of users with similar ages, bone densities, diets, and the like. A training data set for an osteoporosis state machine learning model may be selected according to a classified cohort of users. Training data may be received from previous iterations of osteoporosis state determinations and/or from one or more user inputs such as without limitation inputs provided by one or more experts, such as medical professionals, medical researchers, or the like. In some embodiments, training data may be received through user input of computing device 112, such as, but not limited to, input by an osseous tissue expert or other user. Computing device 112 may utilize a machine-learning model to generate current osteoporosis state 120 of user 104. A "current osteoporosis state" as used in this disclosure is any stage of osteoporosis of an individual. In some embodiments, current osteoporosis state 120 may include, but is not limited to, stage one, stage two, stage three, stage four, and/or any combination thereof. In some embodiments, current osteoporosis state 120 may include an osteoporosis type, such as, but not limited to, type 1 and/or type 2. Type 1 osteoporosis may include postmenopausal osteoporosis. Type 2 osteoporosis may include senile osteoporosis.

In some embodiments, current osteoporosis state 120 may include a precursor state. A "precursor state" as used in this disclosure is any state of a user in which the user is prone to developing osteoporosis in the future. In some embodiments, a precursor state may include, but is not limited to, a percent risk, probability, or other metric of a user potentially developing some form of osteoporosis. In a non-limiting example, computing device 112 may generate current osteoporosis state 120 indicating user 104 is in a precursor state with a 14% probability of developing osteoporosis within two years.

Still referring to FIG. 1, in some embodiments, computing device 112 may include an osteoporosis classifier. An "osteoporosis classifier" as used in this disclosure is a classifier as described in further detail below that identifies one or more types of osteoporosis. Computing device 112 and/or prediction engine 124 may use an osteoporosis classifier to determine a type of osteoporosis. An osteoporosis identifier may be trained with a set of training data correlating osteoporosis data to categories and/or subcategories of osteoporosis, such as, but not limited to, mild, moderate, severe, stage one, stage two, stage three, stage four, and the like. Training data may be received from iterative classification of an osteoporosis classifier and/or received from one or more user at computing device 112. Current osteoporosis state 120 may include an osteoporosis type identified by an osteoporosis classifier. An osteoporosis classifier may identify a form of osteoporosis as a function of any or all data described above.

Still referring to FIG. 1, computing device 112 may be configured to generate predicated advancement of osteoporosis 128 through prediction engine 124. Prediction engine 124 may include an osteoporosis advancement machine learning model. An osteoporosis advancement machine learning model may be configured to input osseous tissue data and output a predicted advancement of osteoporosis. An osteoporosis advancement machine learning model may be trained on one or more sets of training data. Training data for an osteoporosis advancement machine learning model may correlate states of osteoporosis and/or osseous tissue data to predicted advancements of osteoporosis. Training data may be received from previous iterations of predicted advancements of osteoporosis. In some embodiments, training data may be received from an osseous tissue expert or other user through computing device 112. A machine learning model may be described in further detail below with reference to FIG. 4. Prediction engine 124 may be configured to input osseous tissue data 116, current osteoporosis state 120, and output predicted advancement of osteoporosis 128. A "predicted advancement of osteoporosis" as used in this disclosure is any calculated progression of osteoporosis in an individual. In some embodiments, predicted advancement of osteoporosis 128 may include a predicted stage of osteoporosis. In other embodiments, predicted advancement of osteoporosis 128 may include symptoms such as, but not limited to, reduced bone density, increased likelihood of fracture, increased likelihood of breaking, decreased likelihood of fracture, decreased likelihood of breaking, increased mobility, decreased mobility, and the like. In some embodiments, predicted advancement of osteoporosis 128 may include a prediction of a specific bone of user 104. In a non-limiting example, prediction engine 124 may generate predicted advancement of osteoporosis 128 which may include a likelihood of a wrist fracture of user 104.

Still referring to FIG. 1, in some embodiments, predicted advancement of osteoporosis 128 may include a percent risk for developing one or more future stages of osteoporosis. A percent risk for developing future stages of osteoporosis may include a probability, which may be expressed without limitation as a percentage, of developing one or more symptoms of one or more stages of osteoporosis. In some embodiments, a percent risk for developing future stages of osteoporosis may include a precursor stage. In a non-limiting example, a percent risk for developing future stages of osteoporosis may include a 9% risk of developing stage one osteoporosis within 12 months. In some embodiments, a percent risk for developing future stages of osteoporosis may include a percent risk based on current states of user 104. In some embodiments, a percent risk for developing future stages of osteoporosis may include a percent risk based on user 104 engaging in a recovery program, user 104 partially engaging in a recovery program, and/or user 104 untreated.

Still referring to FIG. 1, predicted advancement of osteoporosis 128 may include a probability of bone loss. A probability of bone loss may include a quantity or proportion of likely bone mass lost. In a non-limiting example, a probability of bone loss may show a user has a 32% probability of losing 12 g of osseous tissue in their foot. In some embodiments, a probability of bone loss may include a bone loss rate. In a non-limiting example, a probability of bone loss may show a user may have a 60% chance of losing 4% of their rib bone mass a year.

Still referring to FIG. 1, predicted advancement of osteoporosis 128 may include a probability of bone fracture. A probability of bone fracture may include a percent probability of fracturing one or more bones. In some embodiments, a probability of bone fracture may be specific to a certain bone or group of bones. In a non-limiting example, a probability of bone fracture may show that a user has a 52% chance of fracturing their hip bone. In another non-limiting example, a probability of bone fracture may show that a user has a 2% chance of fracturing their pinky bone. In some embodiments, a probability of bone fracture may be adjusted based on a current state of user 104. In some embodiments, a probability of bone fracture may show a probability of fracturing a bone if user 104 does not engage in a recovery program. In other embodiments, a probability of bone fracture may include a probability of fracturing a bone if user 104 does engage in a recovery program.

Still referring to FIG. 1, in some embodiments, predicted advancement of osteoporosis 128 may include a probability of developing osteoporosis stages and/or symptoms over a timeline. In some embodiments, osteoporosis stages may include a first stage of osteoporosis. A "first stage of osteoporosis" as used in this disclosure is a rate of bone deposition about equal to a breakdown rate of a bone in an individual. In some embodiments, a first stage of osteoporosis may include a T score of −1.0 or higher. A "T score" is the bone mineral density at the site when compared to the young normal reference mean, which is a BMD of a healthy 30 year old. A first stage of osteoporosis may include ages of individuals between 30 to 35. A first stage of osteoporosis may include an equilibrium of bone deposition and bone breakdown, which may reduce bone mineral density. A first stage of osteoporosis may be referred to as "leaching". In some embodiments, a timeline may include, but is not limited to, days, weeks, months, years, decades, and the like. In some embodiments, a probability of developing osteoporosis stages and/or symptoms may show specific probabilities at specific points in time. In a non-limiting example, a probability of developing osteoporosis stages and/or symptoms over a timeline may show a user has a 12% probability of entering stage one osteoporosis at age 49, a 34% probability of fracturing a wrist bone at age 65, and a 70% probability of losing 8% of cortical bone mass by age 90.

Still referring to FIG. 1, predicted advancement of osteoporosis 128 may include a decreasing probability of developing osteoporosis with treatment. A decreasing probability of developing osteoporosis with treatment may include a percent of recovering from one or more symptoms and/or one or more stage of osteoporosis. In a non-limiting example, a decreasing probability of developing osteoporosis may show that a user has a 3% of developing stage two osteoporosis compared to a prior 14% probability of developing stage two osteoporosis.

Still referring to FIG. 1, predicted advancement of osteoporosis 128 may include an estimated time until developing one or more symptoms and/or one or more stages of osteoporosis. An estimated timeline may include, but is not limited to, days weeks, months, years, decades, and the like. In some embodiments, an estimated time until developing one or more symptoms may include a specific date at which user 104 may develop symptoms of osteoporosis. In a non-limiting example, predicted advancement of osteoporosis 128 may show that a user has an 80% chance of developing stage three osteoporosis by Jun. 4, 2060. In some embodiments, an estimated time until developing one or more symptoms may include a general range of times a user may develop symptoms. In a non-limiting example, an estimated time until developing one or more symptoms may show that a user has about three months until they have a 90% chance of fracturing their ankle.

Still referring to FIG. 1, predicted advancement of osteoporosis 128 may include a confidence level of one or more osteoporosis related predictions of predicted advancement of osteoporosis 128. In a non-limiting example, predicted advancement of osteoporosis 128 may show that user 104 has a 34% chance of developing stage one osteoporosis with a 91% confidence score of the prediction. Continuing this example, predicted advancement of osteoporosis 128 may also show a decrease to 4% chance of a user developing stage one osteoporosis with treatment. Predicted advancement of osteoporosis 128 may show a confidence score of reducing chances of developing stage one osteoporosis with treatment of 87%. Predicted advancement of osteoporosis 128 may include a projected timeline of developing and/or reversing osteoporosis for a user. In a non-limiting example, predicted advancement of osteoporosis 128 may show a 57 year old user is increasing likely to develop osteoporosis with an estimated probability of developing osteoporosis of 28% at ages 58-61, 46% at ages 62-80, and 55% at ages 80 and above. Any or all data about user 104 as described above may be used as input to any or all machine learning models described throughout this disclosure that may produce predictions of osteoporosis stages, symptoms, development, and the like. Predictions of osteoporosis may be based on any or all user data as described above.

Still referring to FIG. 1, computing device 112 may be configured to generate osteoporosis recovery program 132. An "osteoporosis recovery program" as used in this disclosure is any step or set of steps aimed at reducing and/or reversing osteoporosis relating afflictions of an individual. Osteoporosis recovery program 132 may include, but is not limited to, an exercise regime, diet adjustment, drug regime, and the like. An exercise regime may include a weigh-lifting exercise, which may increase a bone density of user 104. In some embodiments, a diet adjustment may include increasing a consumption of nutrients such as vitamin D and calcium. A drug regime may include, but is not limited to, non-nitrogen-containing bisphosphonates, nitrogen-containing bisphosphonates, conjugated estrogen-progestin hormone replacement, estrogen-only replacement, testosterone, salmon calcitonin, raloxifene, teriparatide, denosumab, romosozumab, and/or other drug treatments. In some embodiments, osteoporosis recovery program 132 may be generated as a function of predicted advancement of osteoporosis 128. As a non-limiting example, user 104 may have a predicted advancement of osteoporosis in a form of a hip fracture. Osteoporosis recovery program may include hip exercises and/or an increase in calcium to fortify the hip area of user 104.

Still referring to FIG. 1, computing device 112 may be configured to generate an optimization problem to select a recovery program from a plurality of available recovery programs from third party providers. Computing device 112 may generate an objective function to compare recovery programs of two or more available recovery programs. An "objective function" as used in this disclosure is a process of maximizing or minimizing one or more values based on a set of constraints. Computing device 112 may use one or more objective functions to maximize or minimize one or more outputs of a machine learning model. In some embodiments, computing device 112 may include an exercise classifier. "An exercise classifier" as used in this disclosure is any process that categorizes exercise data into one or more groups. An exercise classifier may communicate with an exercise database. An exercise database may include a plurality of exercise data, such as, but not limited to, types of exercises, categories of exercise, exercise routines, and the like. An exercise classifier may be trained with a set of training data correlating exercise data to categories of exercise. Training data may be received from previous iterations of an exercise classifier and/or received from one or more users on computing device 112. In some embodiments, an exercise classifier may be configured to categorize one or more forms of exercise into one or more subcategories of exercise, such as, but not limited to, weightlifting, cardio, swimming, anabolic training, anerobic training, high-intensity interval training, compound movements, isolation exercises, and the like. In some embodiments, computing device 112 may use an exercise machine-learning model. An exercise machine learning model may be trained with training data correlating a category of exercise to an osteoporosis treating exercise routine. An exercise machine learning model may be trained on training data from previous processes. In some embodiments, training data may be received from one or more users. In some embodiments, an exercise machine learning model may be configured to input an exercise categorized from an exercise classifier, and output an osteoporosis treating exercise routine of that exercise. In a non-limiting example, an exercise classifier may classify exercise data into a strength training category. An exercise machine learning model may input the strength training exercise data and output specific repetitions, sets, variations, forms, and the like for a user to follow in order to treat a form of osteoporosis.

Still referring to FIG. 1, computing device 112 may include a diet classifier. A "diet classifier" as used in this disclosure is any process that categories diet data into groups and/or subgroups. A diet classifier may be in communication with a diet database. A diet database may include nutritional data, food categories, vitamin categories, and the like. A diet classifier may be trained with a set of training data correlating diet data to categories of diets. Training data may be received from previous iterations of a diet classifier and/or received from one or more users at computing device 112. A diet classifier may input diet data and categorize diet data into groups such as, but not limited to, food types, nutritional types, breakfast, lunch, dinner, snacks, and the like. In some embodiments, computing device 112 may include a diet machine learning model. A diet machine learning model may be trained on training data correlating diet data to an osteoporosis treating nutrition plan. Training data may include data from previous iterations of processes described above. In some embodiments, training data may be received from one or more users on computing device 112. A diet machine learning model may input a categorized diet datum from a diet classifier and output an osteoporosis treating nutrition plan. In a non-limiting example, a diet classifier may input a user's daily diet, and categorize the diet into groups such as high calcium, low calcium, high vitamin D, low vitamin D, and the like. A diet machine learning model may input the categorized diet data and output an osteoporosis treating nutrition plan that may include a user consuming more diary.

Still referring to FIG. 1, computing device 112 may include a drug classifier. A "drug classifier" as used in this disclosure is any process that categorizes drugs into groups and/or subgroups, such as, but not limited to, osteoporosis advancing drugs, osteoporosis reducing drugs, and the like. A drug classifier may be in communication with a drug database. A drug database may include data about drugs such as, but not limited to, drug type, drug amounts, drug effects, drug complications, history of use, and the like. A drug classifier may be trained with a set of training data correlating drugs to categories of drugs. Training data may be received from previous iterations of a drug classifier and/or from one or more users at computing device 112. A drug classifier may be configured to input drug data and output one or more categories and/or subcategories of drug, such as, but not limited to, osteoporosis advancing, osteoporosis reducing, and the like. In some embodiments, computing device 112 may use a drug machine learning model. A drug machine learning model may be trained on training data correlating drug data to an osteoporosis reducing drug plan. Training data may be received from previous iterations of processing and/or from one or more users. In some embodiments, a drug machine learning model may be configured to input a drug and output an effect the drug has on osteoporosis. In some embodiments, a drug machine learning model may be configured to input data from a drug classifier and output an effect one or more drugs have on osteoporosis of a user. In a non-limiting example, a drug classifier may categorize alcohol as an osteoporosis advancing drug, and a drug machine learning model may input the alcohol and output a plan of reducing alcohol consumption.

Still referring to FIG. 1, in some embodiments computing device 112 may include a medication classifier. A "medication classifier" as used in this disclosure is any process of categorizing medications to groups and/or subgroups. In some embodiments, a medication classifier may input medication data and output a category of medication, such as, but not limited to, osteoporosis advancing drugs, osteoporosis reducing drugs, and the like. A medication classifier may be in communication with a medication database. A medication database may include data about medications such as, but not limited to, medication types, medication amounts, medication effects, history of medications, and the like. A medication classifier may be trained with a set of training data correlating medication data to categories and/or subcategories of medication such as, but not limited to, medication class, medication side effects, medication effect on osteoporosis, and the like. Training data may be received from previous iteration of a medication classifier and/or from one or more users at computing device 112. In some embodiments, computing device 112 may include a medication machine learning model. A medication machine learning model may be trained on a set of training data correlating medication data to osteoporosis advancements. In some embodiments, training data may be received from iterative processing of a medication machine learning model. In some embodiments, training data may be received by one or more users. A medication machine learning model may be configured to input a plurality of medication data and output a medication regime. In a non-limiting example, a drug classifier may classify Evista® as an osteoporosis reducing drug, and a drug machine learning model may input Evista® and output an amount, duration, and/or schedule of Evista® consumption for a user.

Still referring to FIG. 1, in some embodiments, computing device 112 may include a physical therapy classifier. A "physical therapy classifier" as used in this disclosure is any process that categorizes physical therapy data into categories and/or subcategories. A physical therapy classifier may be trained with a set of training data correlating physical therapy data to one or more categories and/or subcategories of physical therapy, such as, but not limited to, body part specific physical therapy, physical therapy type, and the like. Training data may be received from previous iterations of a physical therapy classifier and/or from one or more users at computing device 112. In some embodiments, a physical therapy classifier may be in communication with a physical therapy database. A physical therapy database may include a plurality of data of physical therapy, such as, but not limited to, types of physical therapy, body part specific physical therapy, physical therapy costs, physical therapy effectiveness, and the like. In some embodiments, a physical therapy classifier may classify physical therapy data into categories such as, but not limited to, physical therapy type, physical therapy price, body part specific physical therapy, and the like. In some embodiments, computing device 112 may include a physical therapy machine learning model. A physical therapy machine learning model may be trained on training data correlating physical therapy to osteoporosis treatment. Training data may be received from iterative processing of a physical therapy machine learning model. Training data may be received from one or more users on computing device 112. In some embodiments, a physical therapy machine learning model may be configured to input a plurality of physical therapy data and output a physical therapy regime. In some embodiments, a physical therapy machine learning model may be configured to input categorized physical therapy data from a physical therapy classifier. In a non-limiting example, a physical therapy classifier may classify a physical therapy to a group of elbow therapy. A physical therapy machine learning model may input the elbow therapy and output a physical therapy treatment regime for an elbow which may include, but is not limited to, costs, frequencies, durations, movements, and the like.

Still referring to FIG. 1, in some embodiments, computing device 112 may use any or all of the above classifiers and/or machine learning models to generate an objective function. In some embodiments, any or all of the above classifiers and/or machine learning models may output warnings where a user should seek medical help from a medical professional. In some embodiments, user 104 may input one or more limitations and/or preferences into computing device 112, which may adjust any or all of the above classifiers and/or machine learning models. In some embodiments, user 104 may input limitations and/or preferences into computing device 112 and receive osteoporosis recovery program 132 which may be adjusted based on the limitations and/or preferences. This may occur any number of times, to generate "what if" scenarios for user 104. In some embodiments, an objective function generated by computing device 112 may include an optimization criterion. An optimization criterion may include any description of a desired value or of values for one or more attributes of a recovery program; desired value or range of values may include a maximal or minimal value, a range between maximal or minimal values, or an instruction to maximize or minimize an attribute. As a non-limiting example, an optimization criterion of at least an optimization criterion may specify that a recovery program should not be costly; an optimization criterion may cap costs of a recovery program. An optimization criterion may specify one or more thresholds for recovery programs. An optimization criterion may specify one or more desired providers of recovery programs. In an embodiment, at least an optimization criterion may assign weights to different attributes or values associated with attributes; weights, as used herein, may be multipliers or other scalar numbers reflecting a relative importance of a particular attribute or value. As a non-limiting example, minimization of cost may be multiplied by a first weight, while a preferred provider ranking above a certain value may be multiplied by a second weight. Optimization criteria may be combined in weighted or unweighted combinations into a function reflecting an overall outcome desired by a user; function may be a recovery program function to be minimized and/or maximized. Function may be defined by reference to cost constraints and/or weighted aggregation thereof; for instance, a recovery program function combining optimization criteria may seek to minimize or maximize a function of cost constraints.

Still referring to FIG. 1, computing device 112 may use an objective function to compare a recovery program to another recovery program. Generation of an objective function may include generation of a function to score and weight factors to achieve a score for each feasible pairing. In some embodiments, pairings may be scored in a matrix for optimization, where columns represent recovery programs and rows represent costs potentially paired therewith; each cell of such a matrix may represent a score of a pairing of the corresponding recovery program to the corresponding cost. In some embodiments, assigning a predicted process that optimizes the objective function includes performing a greedy algorithm process. A "greedy algorithm" is defined as an algorithm that selects locally optimal choices, which may or may not generate a globally optimal solution. For instance, computing device 112 may select pairings so that scores associated therewith are the best score for each order and/or for each process. In such an example, optimization may determine the combination of processes such that each object pairing includes the highest score possible.

Still referring to FIG. 1, an objective function may be formulated as a linear objective function. Computing device 112 may solve an objective function using a linear program such as without limitation a mixed-integer program. A "linear program," as used in this disclosure, is a program that optimizes a linear objective function, given at least a constraint. For instance, and without limitation, objective function may seek to maximize a total score $\Sigma_{r \in R} \Sigma_{s \in S} c_{rs} x_{rs}$, where R is a set of all recovery programs r, S is a set of all costs s, $c_{rs}$ is a score of a pairing of a given recovery program with a given cost, and $x_{rs}$ is 1 if a recovery program r is paired with a cost s, and 0 otherwise. Continuing the example, constraints may specify that each recovery program is assigned to only one cost, and each cost is assigned only one recovery program. Recovery programs may be as described above. Sets of recovery programs may be optimized for a maximum score combination of all generated recovery programs. In various embodiments, computing device 112 may determine a combination of recovery programs that maximizes a total score subject to a constraint that all recovery programs are paired to exactly one cost. In some embodiments, not all recovery programs may receive a cost pairing since each communication may only use one recovery program. In some embodiments, an objective function may be formulated as a mixed integer optimization function. A "mixed integer optimization" as used in this disclosure is a program in which some or all of the variables are restricted to be integers. A mathematical solver may be implemented to solve for the set of feasible pairings that maximizes the sum of scores across all pairings; mathematical solver may be implemented on computing device 112 and/or another device in system 100, and/or may be implemented on third-party solver.

With continued reference to FIG. 1, optimizing an objective function may include minimizing a loss function, where a "loss function" is an expression an output of which an optimization algorithm minimizes to generate an optimal result. As a non-limiting example, computing device 112 may assign variables relating to a set of parameters, which may correspond to a score of recovery programs as described above, calculate an output of mathematical expression using the variables, and select a pairing that produces an output having the lowest size, according to a given definition of "size," of the set of outputs representing each of plurality of candidate ingredient combinations; size may, for instance, included absolute value, numerical size, or the like. Selection of different loss functions may result in identification of different potential pairings as generating minimal outputs. Objectives represented in an objective function and/or loss function may include minimization of costs. Objectives may include minimization of recovery time. Objectives may include minimization of waiting time. Objectives may include minimization of side effects. Objectives may include minimization of osteoporosis advancement.

Still referring to FIG. 1, computing device 112 may be configured to transmit osteoporosis recovery program 132 to remote computing device 136. Remote computing device 136 may include, but is not limited to, a smartphone, tablet, desktop, laptop, server, and the like. In some embodiments, computing device 112 may communicate osteoporosis recovery program 132 through a mobile application. In some embodiments, remote computing device 136 may include a computing device of user 104. Remote computing device 136 may be configured to display osteoporosis recovery program 132, predicted advancement of osteoporosis 128, osseous tissue data 116, current osteoporosis state 120, and/or other data pertaining to user 104. In some embodiments, remote computing device 136 may be configured to set reminders for user 104 to adhere to osteoporosis recovery program 132. In some embodiments, reminders may include, but are not limited to, exercise reminders, diet reminders, drug reminders, and the like. In some embodiments, reminder may alert user 104 based on a schedule of osteoporosis recovery program 132. In some embodiments, remote computing device 136 may alert user 104 of a predicted advancement of osteoporosis 128. In a non-limiting example, remote computing device 136 may alert user 104 that rib fracture may be predicted to occur. In some embodiments, remote computing device 136 may be configured to generate physiological data 140. "Physiological data" as used in this disclosure is any data relating to a biology of an individual. In some embodiments, physiological data 140 may include, but is not limited to, diets habits, exercise habits, adherence to osteoporosis recovery program 132, and the like. In some embodiments, physiological data 140 may include risk factors for osteoporosis advancement of user 104. Risk factors may include, but are not limited to, sedentary lifestyle, being a Caucasian woman of northern European descent, smokers, low body weight, low protein intake, heavy drinking, family history of osteoporosis, premature menopause, breast feeders with low vitamin D diets, malabsorption syndromes, liver disease, hyperthyroidism, type I diabetes mellitus, cancer, chronic renal failure, COPD, rheumatoid arthritis, sarcoidosis, and/or other factors. In some embodiments, risk factors may include genetic polymorphisms, such as, but not limited to, calcitonin receptor, estrogen receptor-1, type 1 collagen alpha-1 chain, vitamin D receptor, LRP5, and/or other genetic polymorphisms. In some embodiments, risk factors may include medications, such as, but not limited to, phenytoin, cytotoxic/antineoplastic drugs, SSRI's, antiretroviral therapy, cyclosporine, furosemide, high dose methotrexate, over supplementation of levothyroxine, omeprazole, glucocorticoids, unfractionated heparin and LMWH, vitamin A, thiazolidinediones, and/or other medications. Remote computing device 136 may be configured to obtain risk factors from user 104 through user input. In some embodiments, remote computing device 136 may be configured to connect to an osteoporosis data network. An "osteoporosis data network" as used in this disclosure is any system of osseous related devices, entities, and/or experts. An osteoporosis data network may include a healthcare provider network. In some embodiments, computing device 112 may communicate with an osteoporosis data network to find "best match" options for outputs of any or all machine learning models as described above. In some embodiments, computing device 112 may use a second objective function to find a "best match" for one or more options available on an osteoporosis data network. A second objection function may be configured to minimize a difference between a selected "best match" available from an osteoporosis network and recovery program 132. In some embodiments, remote computing device 136 may record an adherence to osteoporosis recovery program 132. In some embodiments, recording an adherence to osteoporosis recovery program 132 may include recording dates, days, times, and the like. In some embodiments, recording an adherence to osteoporosis recovery program 132 may include recording a completion of one or more steps of osteoporosis recovery program 132, such as, but not limited to, exercise, nutrient consumption, drug intake, and the like. Remote computing device 132 may be configured to generate physiological data 140 as a function of any of the above data points.

Still referring to FIG. 1, remote computing device 132 may be configured to transmit physiological data 140 to computing device 112. Computing device 112 may use physiological data 140 to update osteoporosis recovery program 132. In some embodiments, computing device 112 may input osseous tissue data 116, current osteoporosis state 120, and physiological data 140 into prediction engine 124. Prediction engine 124 may be configured to output predicted advancement of osteoporosis 128 and osteoporosis recovery program 132 as a function of osseous tissue data 116, current osteoporosis state 120, and physiological data 140. In some embodiments, prediction engine 124 may be configured to receive additional input variables such as, but not limited to, user input, doctor input, user history, new treatments of osteoporosis, and the like. Computing device 112 may be configured to generate an osseous tissue data extraction template. An "osseous tissue data extraction template" as used in this disclosure is any guide for osseous tissue data collection. In some embodiments, computing device 112 may generate an osseous tissue data extraction template for an osseous tissue expert, such as a doctor. Computing device 112 may use physiological data 140, osseous tissue data 116, and/or current osteoporosis state 120 to generate an osseous tissue data extraction template. An osseous tissue data extraction template may include, but is not limited to, a bone scan, weight measurement, nutrient analysis, blood sample analysis, mobility measurements, and the like. Computing device 112 may automatically generate an osseous tissue data extraction template for an osseous expert based on data of user 104. By automatically generating an osseous tissue data extraction template for an osseous expert, computing device 112 may reduce clinical checkup times.

Figure 2:
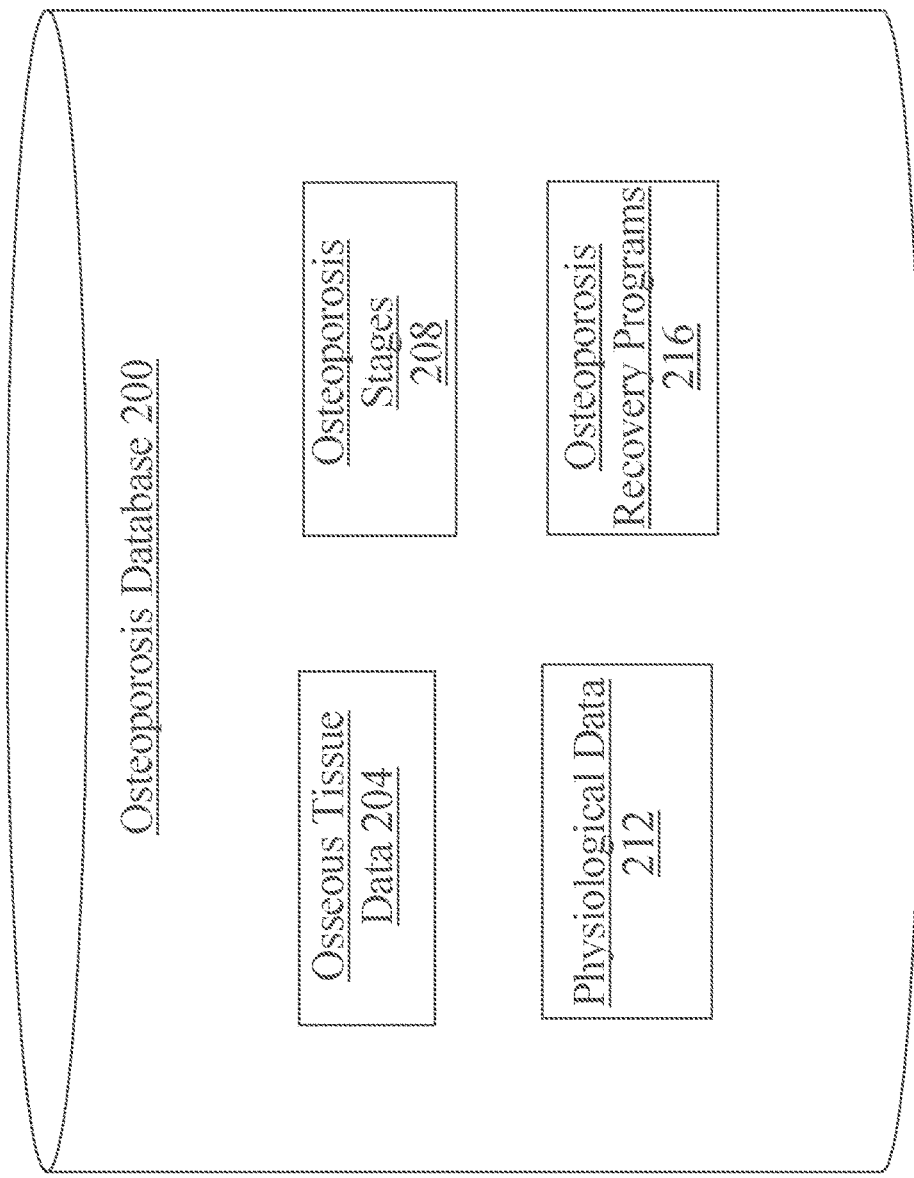
FIG. 2 is an exemplary embodiment of an osteoporosis database.

Referring now to FIG. 2, osteoporosis database 200 is shown. Osteoporosis database 200 may be in communication with computing device 112. In some embodiments, osteoporosis database 200 may be configured to communicate with an osteoporosis data network. Database may be implemented, without limitation, as a relational database, a key-value retrieval database such as a NOSQL database, or any other format or structure for use as a database that a person skilled in the art would recognize as suitable upon review of the entirety of this disclosure. Database may alternatively or additionally be implemented using a distributed data storage protocol and/or data structure, such as a distributed hash table or the like. Database may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

Still referring to FIG. 2, in some embodiments, osteoporosis database 200 may include osseous tissue data 204. Osseous tissue data 204 may include osseous tissue data from a plurality of individuals and/or users. In some embodiments, osseous tissue data 204 may include, but is not limited to, bone density, bone weight, bone strength, bone fragility, bone brittleness, bone structure, bone hollowness, and the like. Osteoporosis database 200 may be configured to categorize osseous tissue data 204 into a category. A category may include, but is not limited to, age, height, weight, risk factors, T score, and the like. In some embodiments, osseous tissue data 204 may be sorted into categories of stages of osteoporosis, such as a first, second, third, and/or fourth stage etc. In some embodiments, osteoporosis tissue data 204 may be categorized by severity. In a non-limiting example, osseous tissue data 204 may include data of a 65 year old woman with multiple previous bone fractures. Osteoporosis database 200 may categorize this data as severe. In another non-limiting example, osseous tissue data 204 may include data of a 20 year old man with no risk factors and high bone density. This data may be categorized as mild. In some embodiments, osteoporosis database 200 may be configured to receive osseous tissue data 204 from computing device 112.

Still referring to FIG. 2, in some embodiments, osteoporosis database 200 may include osteoporosis stages 208. Osteoporosis stages 208 may include a plurality of stages of osteoporosis and related symptoms and treatments. In some embodiments, osteoporosis stages 208 may include a first stage of osteoporosis. A first stage of osteoporosis may be defined by a slowing rate of bone deposition to about equal a breakdown rate of a bone. A first stage of osteoporosis may include a T score of −1.0 or higher. A "T score" is the bone mineral density at the site when compared to the young normal reference mean, which is a BMD of a healthy 30 year old. A first stage of osteoporosis may include ages of individuals between 30 to 35. A first stage of osteoporosis may include an equilibrium of bone deposition and bone breakdown, which may reduce bone mineral density. A first stage of osteoporosis may be referred to as "leaching". In some embodiments, osteoporosis stages 208 may include a second stage of osteoporosis. A second stage of osteoporosis may include ages of individuals between 25 and 35. A second stage of osteoporosis may include a T score of between −1.0 to −2.5. A second stage of osteoporosis may be defined as when a rate of bone breakdown outweighs a rate of bone deposition. In a second stage of osteoporosis, bone loss may begin to occur at about a rate of 0.25% a year. In some embodiments, osteoporosis stages 208 may include a third stage of osteoporosis. A third stage may include a T score of −2.5 or lower, which may indicate a bone density that is two and a half standard deviations below the mean of a 30 year old. A third stage may include an increased chance of bone fracture and/or bone breaking. In some embodiments, osteoporosis stages 208 may include a fourth stage. A fourth stage may be defined as significant, visible bone loss. A fourth stage may include softening of bones and accumulated fragility fractures, resulting in deformity. A fourth stage may include anterior wedging of vertebral bodies of the spine, causing a rounded bent over appearance. A fourth stage may include an age of individuals over 64.

Still referring to FIG. 2, osteoporosis database 200 may include physiological data 212. Physiological data 212 may include data such as, but not limited to, age, weight, height, diet, exercise, nutrient consumption, risk factors, family history, and the like. Physiological data 212 may include a plurality of physiological data from a plurality of individuals and/or users.

Still referring to FIG. 2, osteoporosis database 200 may include osteoporosis recovery programs 216. Osteoporosis recovery programs 216 may include osteoporosis treatments such as, but not limited to, exercise regimes, diet regimes, drug regimes, and the like. Osteoporosis recovery programs 216 may include a plurality of recovery programs from a plurality of individuals and/or users. In some embodiments, osteoporosis recovery programs 216 may include a success rate of recovering from osteoporosis. In some embodiments, osteoporosis recovery programs 216 may include a program correlated to a specific stage of osteoporosis, physiological data, osseous tissue data, and the like.

Figure 3:
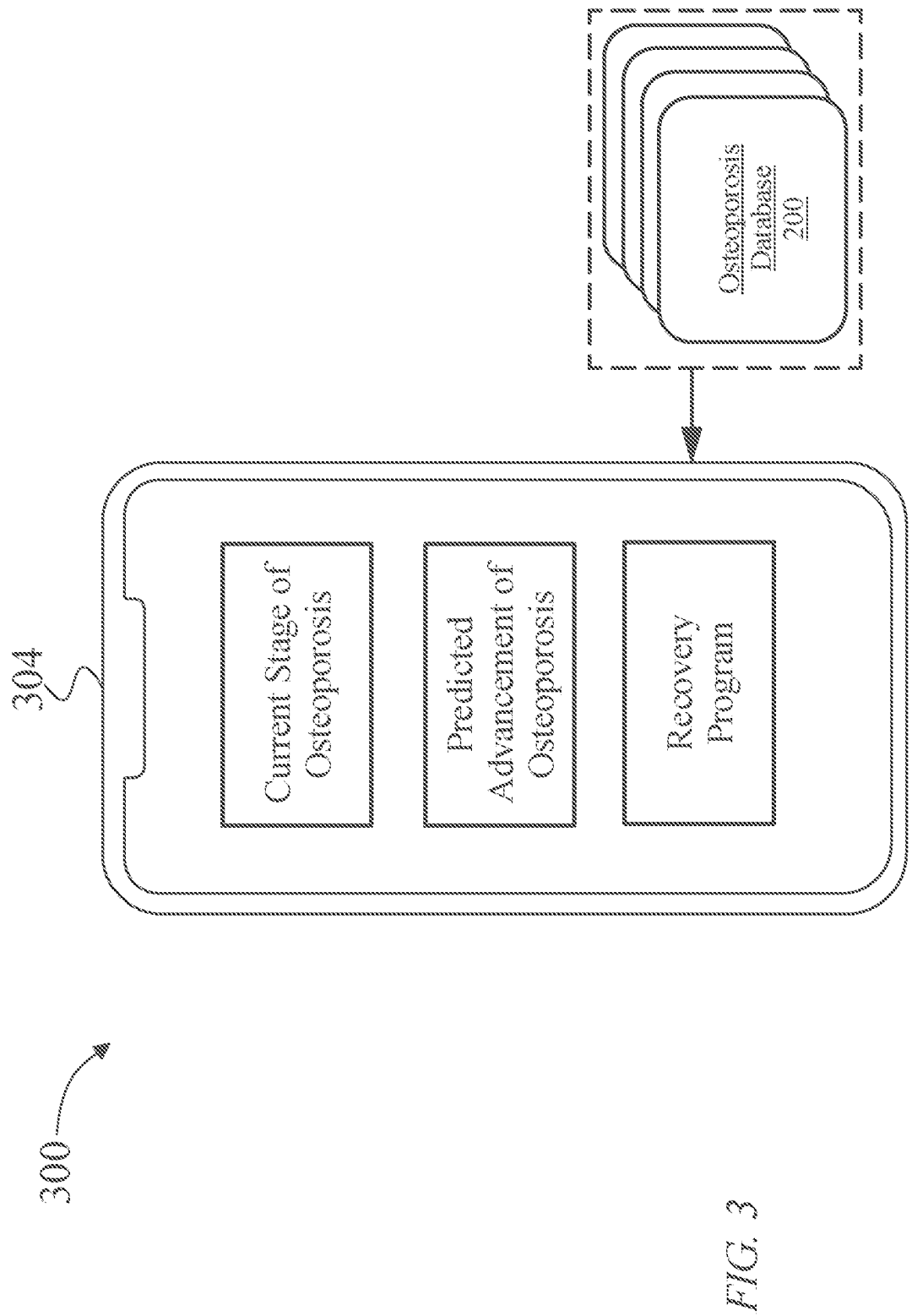
FIG. 3 is a diagram of a GUI according to an embodiment of the invention.

Referring now to FIG. 3, a GUI 300 of an osteoporosis monitoring system is shown. GUI 300 may be configured to be displayed on remote computing device 304. Remote computing device 304 may include, but is not limited to, a smartphone, tablet, desktop, laptop, and the like. In some embodiments, remote computing device 304 may be configured to communicate with computing device 112. In some embodiments, remote computing device 304 may be configured to communicate with osteoporosis database 200. GUI 300 be configured to be displayed on a touch screen. In some embodiments, GUI 300 may be configured to be interactive. GUI 300 may be configured to interact with a user to record physiological data, adherence to a recovery program, reminders for steps of a recovery program, and the like. In some embodiments, GUI 300 may be configured to display a questionnaire. A questionnaire may include one or more questions relating to physiological data of a user such as, but not limited to, age, sex, height, weight, smoking, drinking, family history, risk factors, and the like. In some embodiments, GUI 300 may be configured to display a current stage of osteoporosis to a user. A current stage of osteoporosis may include a T score, BMD, stage classification, and the like. In some embodiments, a current stage of osteoporosis may include a specific bone of a user, such as, but not limited to, a wrist bone, hip bone, vertebrae, leg bone, and the like. In some embodiments, GUI 300 may be configured to display a predicted advancement of osteoporosis to a user. GUI 300 may display a likelihood of fracture of a bone, a decreased bone density, and the like. GUI 300 may display an increase in mobility, bone density, decrease in likelihood of fracture, and the like. GUI 300 may be configured to display reminders to a user for one or more steps of a recovery program for the user. In some embodiments, a reminder may include, but is not limited to, a scheduled drug intake, exercise regime, nutrient consumption, and the like.

Figure 4:
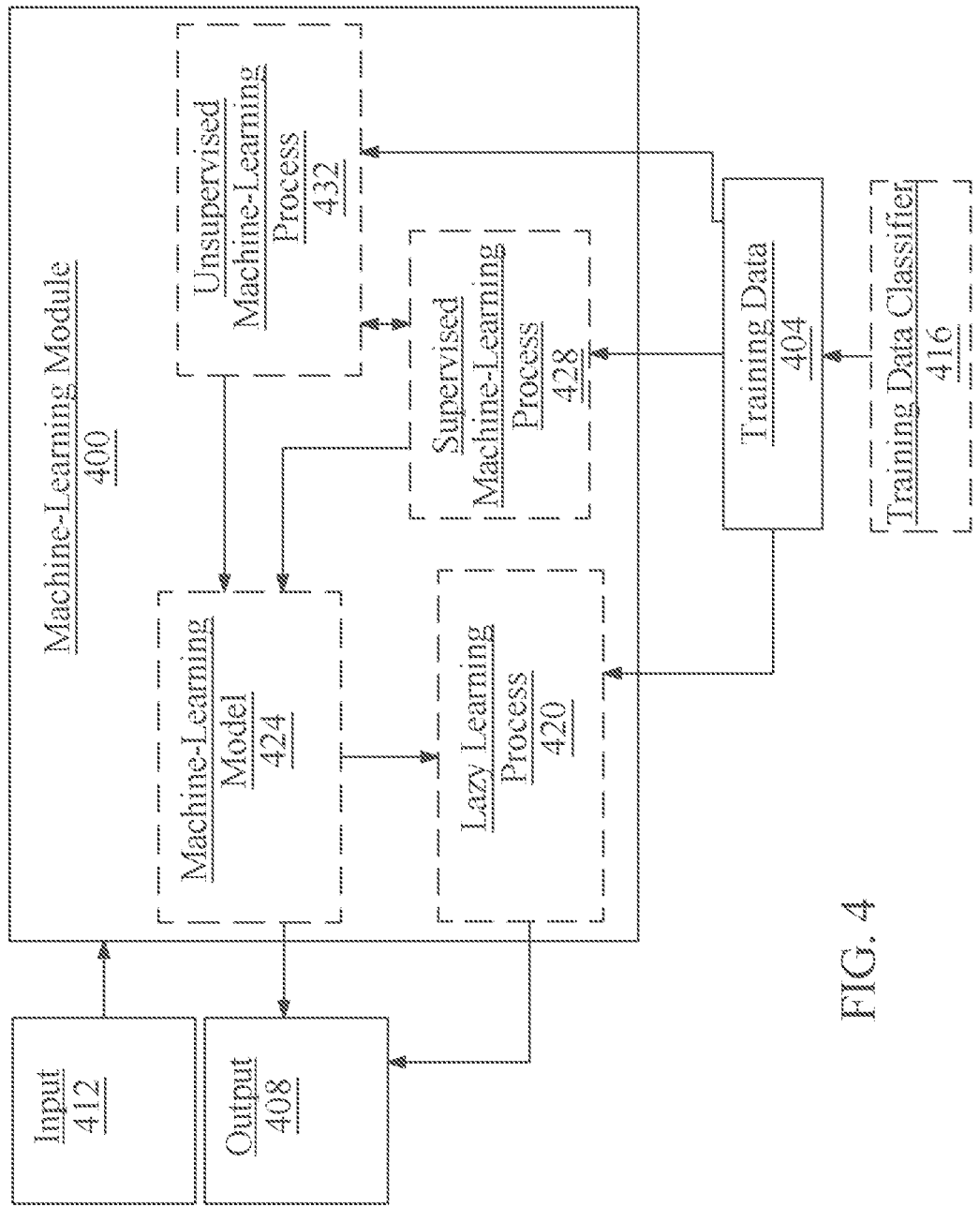
FIG. 4 is a block diagram of an exemplary embodiment of a machine learning model.

Referring now to FIG. 4, an exemplary embodiment of a machine-learning module 400 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 404 to generate an algorithm that will be performed by a computing device/module to produce outputs 408 given data provided as inputs 412; this is in contrast to a non-machine learning software program where the commands to be executed are determined in advance by a user and written in a programming language.

Still referring to FIG. 4, "training data," as used herein, is data containing correlations that a machine-learning process may use to model relationships between two or more categories of data elements. For instance, and without limitation, training data 404 may include a plurality of data entries, each entry representing a set of data elements that were recorded, received, and/or generated together; data elements may be correlated by shared existence in a given data entry, by proximity in a given data entry, or the like. Multiple data entries in training data 404 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 404 according to various correlations; correlations may indicate causative and/or predictive links between categories of data elements, which may be modeled as relationships such as mathematical relationships by machine-learning processes as described in further detail below. Training data 404 may be formatted and/or organized by categories of data elements, for instance by associating data elements with one or more descriptors corresponding to categories of data elements. As a non-limiting example, training data 404 may include data entered in standardized forms by persons or processes, such that entry of a given data element in a given field in a form may be mapped to one or more descriptors of categories. Elements in training data 404 may be linked to descriptors of categories by tags, tokens, or other data elements; for instance, and without limitation, training data 404 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 4, training data 404 may include one or more elements that are not categorized; that is, training data 404 may not be formatted or contain descriptors for some elements of data. Machine-learning algorithms and/or other processes may sort training data 404 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 404 to be made applicable for two or more distinct machine-learning algorithms as described in further detail below. Training data 404 used by machine-learning module 400 may correlate any input data as described in this disclosure to any output data as described in this disclosure. As a non-limiting illustrative example inputs may include osseous tissue data, states of osteoporosis, and physiological data, and outputs may include osteoporosis recovery programs.

Further referring to FIG. 4, training data may be filtered, sorted, and/or selected using one or more supervised and/or unsupervised machine-learning processes and/or models as described in further detail below; such models may include without limitation a training data classifier 416. Training data classifier 416 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 400 may generate a classifier using a classification algorithm, defined as a processes whereby a computing device and/or any module and/or component operating thereon derives a classifier from training data 404. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 416 may classify elements of training data to osteoporosis categories such as bone density, bone strength, bone softening, bone thickness, and the like.

Still referring to FIG. 4, machine-learning module 400 may be configured to perform a lazy-learning process 420 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 404. Heuristic may include selecting some number of highest-ranking associations and/or training data 404 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 4, machine-learning processes as described in this disclosure may be used to generate machine-learning models 424. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 424 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 424 may be generated by creating an artificial neural network, such as a convolutional neural network comprising an input layer of nodes, one or more intermediate layers, and an output layer of nodes. Connections between nodes may be created via the process of "training" the network, in which elements from a training data 404 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 4, machine-learning algorithms may include at least a supervised machine-learning process 428. At least a supervised machine-learning process 428, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include osseous tissue data as described above as inputs, osteoporosis recovery programs as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 404. Persons skilled in the art, upon reviewing the entirety of this disclosure, will be aware of various possible variations of at least a supervised machine-learning process 428 that may be used to determine relation between inputs and outputs. Supervised machine-learning processes may include classification algorithms as defined above.

Further referring to FIG. 4, machine learning processes may include at least an unsupervised machine-learning processes 432. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 4, machine-learning module 400 may be designed and configured to create a machine-learning model 424 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 4, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device may generate a classifier using a classification algorithm, defined as a processes whereby a computing device 104 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, computing device 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A)÷P(B)$, where $P(AB)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-Limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\sum_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Figure 5:
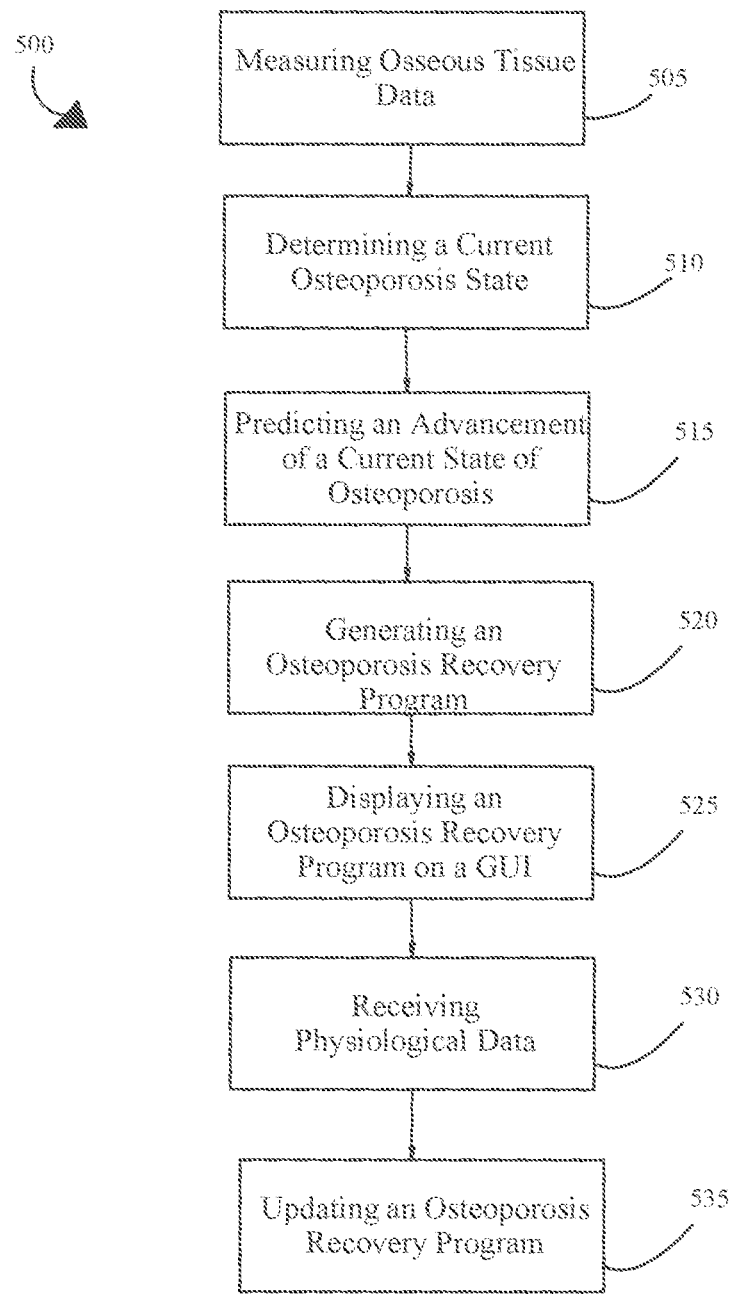
FIG. 5 is a flowchart of a method of osteoporosis monitoring.

Referring now to FIG. 5, a flowchart for method 500 of osteoporosis monitoring is presented. At step 505, method 500 includes measuring osseous tissue data. Osseous tissue data may be measured by a measuring device. In some embodiments, osseous tissue data may be measured by a bone scan, motion detection system, or other method. In some embodiments, osseous tissue data may include, but is not limited to, bone density, bone mobility, bone strength, bone weight, bone fragility, bone brittleness, bone hollowness, and the like. Measuring osseous tissue data may be as described in FIG. 1.

Still referring to FIG. 5, at step 510, method 500 includes determining a current osteoporosis state. An osteoporosis state may be determined by osseous tissue data. A current osteoporosis state may include a stage of osteoporosis. A stage may include, but is not limited to, a first, second, third, and/or fourth stage of osteoporosis. An osteoporosis state may include, but is not limited to, a risk factor of advancing osteoporosis, likelihood of bone fracture, likelihood of bone breakage, and the like. Determining an osteoporosis state may be as described in FIG. 1.

Still referring to FIG. 5, at step 515, method 500 includes predicting an advancement of a current state of osteoporosis. Predicting an advancement may include using a prediction engine. A prediction engine may include a machine learning model. In some embodiments, a predicted advancement of a current state of osteoporosis may include, but is not limited to, increased likelihood of fracture, loss of bone density, loss of bone weight, softening of bones, bone hollowness, and the like. Predicting an advancement of a current state of osteoporosis may be as described in FIG. 1.

Still referring to FIG. 5, at step 520, method 500 includes generating an osteoporosis recovery program. An osteoporosis recovery program may be generated as a function of a predicted advancement of a current state of osteoporosis. In some embodiments, a recovery program may include, but is not limited to, a diet regime, nutrient consumption, exercise regime, drug intake, and the like. In some embodiments, a recovery program may be selected from a plurality of available third party recovery programs. Generating an osteoporosis recovery program may be as described in FIG. 1.

Still referring to FIG. 5, at step 525, method 500 includes displaying an osteoporosis recovery program on a GUI. A GUI may include an interactive GUI. A GUI may be displayed on an external computing device, such as, but not limited to, a smartphone, laptop, desktop, tablet, and the like. A GUI may be configured to display one or more steps of a recovery program. In some embodiments, a GUI may be configured to alert a user of scheduled actions in coherence with a recovery program. Displaying an osteoporosis recovery program on a GUI may be as described in FIGS. 1 and 3.

Still referring to FIG. 5, at step 530, method 500 includes receiving physiological data. Physiological data may be received from a remote and/or external computing device. In some embodiments, physiological data may be received from a user device. In some embodiments, physiological data may include, but is not limited to, height, weight, age, sex, diet, risk factors, family history, genetics, and the like. Receiving physiological data may be as described in FIGS. 1 and 3.

Still referring to FIG. 5, at step 535, method 500 includes updating an osteoporosis recovery program. An osteoporosis recovery program may be updated as a function of physiological data. In some embodiments, an osteoporosis recovery program may be updated based on a determined success of the recovery program for an individual. Updating an osteoporosis recovery program may be as described in FIG. 1.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 6:
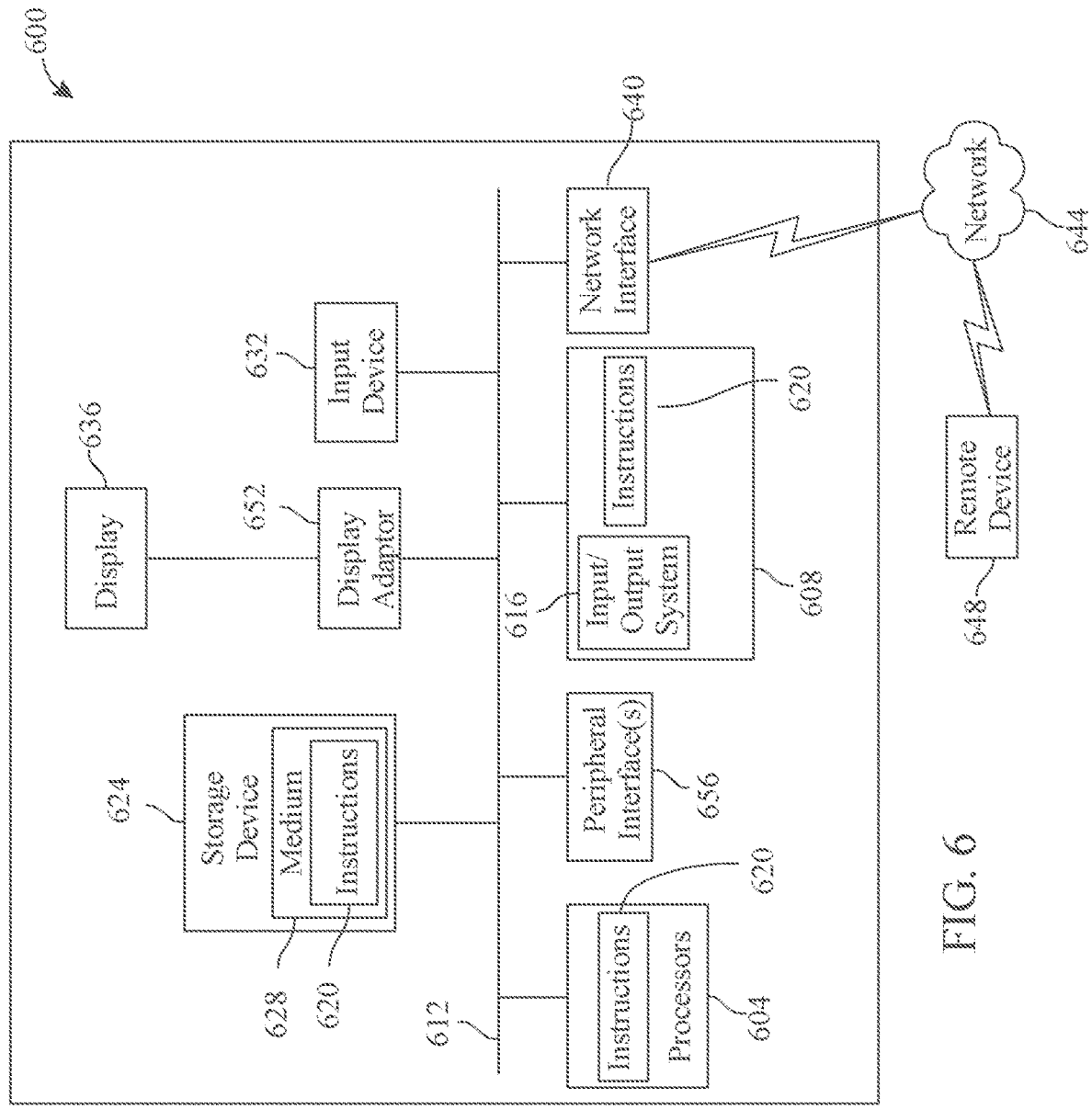
FIG. 6 is a block diagram of a computing system that can be used to implement any one or more of the methodologies disclosed herein and any one or more portions thereof.

FIG. 6 shows a diagrammatic representation of one embodiment of a computing device in the exemplary form of a computer system 600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Still referring to FIG. 6, processor 604 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 604 may be organized according to Von Neumann and/or Harvard architecture as a non-limiting example. Processor 604 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Still referring to FIG. 6, memory 608 may include various components (e.g., machine-readable media) including, but not limited to, a random-access memory component, a read only component, and any combinations thereof. In one example, a basic input/output system 616 (BIOS), including basic routines that help to transfer information between elements within computer system 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system, one or more application programs, other program modules, program data, and any combinations thereof.

Still referring to FIG. 6, computer system 600 may also include a storage device 624. Examples of a storage device (e.g., storage device 624) include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE™), and any combinations thereof. In one example, storage device 624 (or one or more components thereof) may be removably interfaced with computer system 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 600. In one example, software 620 may reside, completely or partially, within machine-readable medium 628. In another example, software 620 may reside, completely or partially, within processor 604.

Still referring to FIG. 6, computer system 600 may also include an input device 632. In one example, a user of computer system 600 may enter commands and/or other information into computer system 600 via input device 632. Examples of an input device 632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIREWIRE™ interface, a direct interface to bus 612, and any combinations thereof. Input device 632 may include a touch screen interface that may be a part of or separate from display 636, discussed further below. Input device 632 may be utilized as a user selection device for selecting one or more graphical representations in a graphical interface as described above.

Still referring to FIG. 6, a user may also input commands and/or other information to computer system 600 via storage device 624 (e.g., a removable disk drive, a flash drive, etc.) and/or network interface device 640. A network interface device, such as network interface device 640, may be utilized for connecting computer system 600 to one or more of a variety of networks, such as network 644, and one or more remote devices 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 644, may employ a wired and/or a wireless mode of communication. In general, any network topology may be used. Information (e.g., data, software 620, etc.) may be communicated to and/or from computer system 600 via network interface device 640.

Still referring to FIG. 6, computer system 600 may further include a video display adapter 652 for communicating a displayable image to a display device, such as display device 636. Examples of a display device include, but are not limited to, a liquid crystal display (LCD), a cathode ray tube (CRT), a plasma display, a light emitting diode (LED) display, and any combinations thereof. Display adapter 652 and display device 636 may be utilized in combination with processor 604 to provide graphical representations of aspects of the present disclosure. In addition to a display device, computer system 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE™ connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for osteoporosis monitoring, comprising:
an osseous measurement device, wherein the osseous measurement device includes an x-ray system, wherein the osseous measurement device is configured to:
 measure osseous tissue data of a user, wherein the osseous tissue data includes bone density data of the user; and
 transmit the osseous tissue data to a computing device, wherein the computing device is configured to:
  determine a current osteoporosis state of the user as a function of the measured osseous tissue data of the user transmitted from the osseous measurement device;
  predict an advancement of the current state of osteoporosis of the user as a function of the osseous tissue data of the user and current osteoporosis state of the user, wherein predicting the advancement of osteoporosis comprises:
   receiving training data, wherein the training data correlates osseous tissue data to stages of osteoporosis, wherein the training data includes results of previous iterations of an osteoporosis advancement machine-learning model and input from an osseous tissue expert;
   training the osteoporosis advancement machine-learning model as a function of the training data; and
   predicting the advancement of the current state of osteoporosis as a function of the osseous tissue data and the osteoporosis advancement machine-learning model, wherein the osseous tissue data and the current osseous state of the user are provided to the trained osteoporosis advancement machine-learning model as inputs to output the predicted advancement of osteoporosis;
  generate, as a function of a prediction engine, an osteoporosis recovery program for the user, wherein the prediction engine is configured to:
   input the predicted advancement of osteoporosis of the user, the measured osseous tissue data of the user, and the current osteoporosis state of the user;
   optimize a selection of an osteoporosis recovery program from a plurality of osteoporosis recovery programs of an osteoporosis network by generating an objective function to compare osteoporosis recovery programs of the plurality of recovery programs; and
   output the osteoporosis recovery program for the user;
  calculate, as a function of the osteoporosis recovery program and the predicted advancement of osteoporosis of the user, a decreased probability of advancing the current osteoporosis state of the user;
  generate, as a function of the osteoporosis recovery program and the predicted advancement of osteoporosis of the user, a confidence score of the decreased probability of advancing the current osteoporosis state of the user;
  display the osteoporosis recovery program and the decreased probability of advancing the current osteoporosis state of the user to the user on an interactive graphical user interface of a remote computing device;
  receive, through the remote computing device, physiological data of the user; and
  update the osteoporosis recovery program as a function of the physiological data of the user and the prediction engine.

2. The system of claim 1, wherein the computing device is further configured to categorize the osseous tissue data into categories of osteoporosis.

3. The system of claim 1, wherein the computing device is further configured to generate an osseous tissue data extraction template as a function of the predicted advancement of osteoporosis of the user.

4. The system of claim 1, wherein the osseous measurement device further comprises a motion sensing system, wherein the motion sensing system is configured to generate the osseous tissue data.

5. The system of claim 1, wherein the remote computing device is configured to communicate with an osteoporosis data network.

6. The system of claim 1, wherein the remote computing device is configured to measure an adherence of the user to the osteoporosis recovery program.

7. The system of claim 1, wherein the osteoporosis recovery program comprises medicinal elements or osseous tissue enhancing nutrients.

8. The system of claim 1, wherein the computing device is further configured to alert the user of the predicted advancement of the current state of osteoporosis through the remote computing device.

9. The system of claim 1, wherein:
the objective function includes at least an optimization criterion;
the at least an optimization criterion includes a plurality of thresholds;
a first threshold of the plurality of thresholds includes a cost threshold for the osteoporosis recovery program; and
a second threshold of the plurality of thresholds includes a ranking threshold for the osteoporosis recovery program.

10. The system of claim 9, wherein:
predicting the advancement of osteoporosis further comprises:
classifying elements of the training data to osteoporosis categories including a training data set classified in a bone density category; and
training the osteoporosis advancement machine-learning model as a function of the training data set; and
the predicted advancement of osteoporosis includes a probability of bone fracture for the user.

11. A method of osteoporosis monitoring, comprising:
measuring, through an osseous tissue measurement device, osseous tissue data of a user, wherein the osseous tissue measurement device includes an x-ray system, wherein the osseous tissue data includes bone density data of the user;
transmitting, through the osseous tissue measurement device, the osseous tissue data of the user to a computing device;
determining, at the computing device, a current osteoporosis state of the user as a function of the osseous tissue data of the user transmitted from the osseous measurement device;
predicting, at the computing device, an advancement of the current state of osteoporosis of the user as a function of the osseous tissue data and the current osteoporosis state of the user, wherein predicting the advancement of osteoporosis further comprises:
receiving training data, wherein the training data correlates osseous tissue data to stages of osteoporosis, wherein the training data includes results of previous iterations of an osteoporosis advancement machine-learning model and input from an osseous tissue expert;
training the osteoporosis advancement machine-learning model with the training data; and
predicting the advancement of the current state of osteoporosis as a function of the osseous tissue data and the osteoporosis advancement machine-learning model, wherein the osseous tissue data and the current osseous state of the user are provided to the trained osteoporosis advancement machine-learning model as inputs to output the predicted advancement of osteoporosis;
generating, at the computing device, an osteoporosis recovery program for the user as a function of a prediction engine, wherein the prediction engine is configured to:
input the predicted advancement of osteoporosis of the user, the measured osseous tissue data of the user, and the current osteoporosis state of the user;
optimize a selection of an osteoporosis recovery program from a plurality of osteoporosis recovery programs of an osteoporosis network by generating an objective function to compare osteoporosis recovery programs of the plurality of recovery programs; and
output the osteoporosis recovery program;
calculating, as a function of the osteoporosis recovery program and the predicted advancement of osteoporosis of the user, a decreased probability of advancing the current osteoporosis state of the user;
generating, as a function of the osteoporosis recovery program and the predicted advancement of osteoporosis of the user, a confidence score of the decreased probability of advancing the current osteoporosis state of the user;
displaying, the osteoporosis recovery program and the decreased probability of advancing the current osteoporosis state of the user to the user on an interactive graphical user interface of a remote computing device;
receiving, through the remote computing device, physiological data of the user; and
updating the osteoporosis recovery program as a function of the physiological data of the user and the prediction engine.

12. The method of claim 11, wherein the computing device is further configured to categorize the osseous tissue data into categories of osteoporosis.

13. The method of claim 11, wherein the computing device is further configured to generate an osseous tissue data extraction template as a function of the predicted advancement of osteoporosis of the user.

14. The method of claim 11, wherein the osseous measurement device further comprises a motion sensing system, wherein the motion sensing system is configured to generate the osseous tissue data.

15. The method of claim 11, wherein the remote computing device is configured to communicate with an osteoporosis data network.

16. The method of claim 11, wherein the remote computing device is configured to measure an adherence of the user to the osteoporosis recovery program.

17. The method of claim 11, wherein the osteoporosis recovery program comprises medicinal elements or osseous tissue enhancing nutrients.

18. The method of claim 11, wherein the computing device is further configured to alert the user of the predicted advancement of the current state of osteoporosis through the remote computing device.

19. The method of claim 11, wherein:
the objective function includes at least an optimization criterion;
the at least an optimization criterion includes a plurality of thresholds;
a first threshold of the plurality of thresholds includes a cost threshold for the osteoporosis recovery program; and
a second threshold of the plurality of thresholds includes a ranking threshold for the osteoporosis recovery program.

20. The method of claim 19, wherein:
predicting the advancement of osteoporosis further comprises:

classifying elements of the training data to osteoporosis categories including a training data set classified in a bone density category; and training the osteoporosis advancement machine-learning model as a function of the training data set; and the predicted advancement of osteoporosis includes a probability of bone fracture for the user.

* * * * *